US00PP27049P3

(12) United States Plant Patent
Skotak, Jr.

(10) Patent No.: US PP27,049 P3
(45) Date of Patent: Aug. 9, 2016

(54) ***GUZMANIA* PLANT NAMED 'DURATAT'**

(50) Latin Name: ***Guzmania* hybrid**
Varietal Denomination: DURATAT

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 107 days.

(21) Appl. No.: 14/121,420

(22) Filed: Sep. 3, 2014

(65) Prior Publication Data

US 2016/0066493 P1 Mar. 3, 2016

(51) Int. Cl.
*A01H 5/00* (2006.01)

(52) U.S. Cl.
USPC ..... Plt./371

(58) Field of Classification Search
USPC ..... Plt./371
See application file for complete search history.

*Primary Examiner* — Annette Para
(74) *Attorney, Agent, or Firm* — Cassandra Bright

(57) ABSTRACT

A new and distinct *Guzmania* cultivar named 'DURATAT' is disclosed, characterized by unusually wide pink-red inflorescence and green leaves. The new variety is a *Guzmania*, typically produced as an indoor ornamental plant.

1 Drawing Sheet

Latin name of the genus and species: *Guzmania* hybrid.
Variety denomination: 'DURATAT'.

BACKGROUND OF THE INVENTION

The new cultivar is a product of a planned breeding program. The objectives of the planned breeding program were to develop new *Guzmania* varieties for commercial ornamental purposes. The new variety originated from a cross pollination of an unnamed, unpatented proprietary *Guzmania* hybrid seed parent with an unpatented, *Guzmania wittmackii* referred to as 'Rosada Purple' as the pollen parent. The crossing was made during 2003 in a commercial greenhouse in Alajuela, Costa Rica.

The new variety was discovered and selected by the inventor, Chester Skotak jr., Jan. 28, 2008 in a group of seedlings resulting from the crossing. The new cultivar was selected in a commercial greenhouse in Alajuela, Costa Rica.

Asexual reproduction of the new cultivar 'DURATAT' was first performed at a commercial laboratory by tissue culture during May of 2011. Subsequent propagation by tissue culture has shown that the unique features of this cultivar are stable and reproduced true to type.

SUMMARY OF THE INVENTION

The cultivar 'DURATAT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DURATAT'. These characteristics in combination distinguish 'DURATAT' as a new and distinct *Guzmania* cultivar:

1. Unusually wide inflorescence.
2. Pink and red inflorescence.
3. Green foliage.

PARENT COMPARISON

Plants of the new cultivar 'DURATAT' are similar to the unpatented seed parent in most horticultural characteristics. The new variety however differs in the following characteristics:

1. Inflorescence is taller and wider than the seed parent.

Plants of the new cultivar 'DURATAT' are similar to the pollen parent, in most horticultural characteristics. The new variety however differs in the following characteristics:

1. Different flower color.
2. Different flower shape.

COMMERCIAL COMPARISON

'DURATAT' can be compared to the commercial variety of *Guzmania* know as 'Allura', patent pending. Plants of the two *Guzmania* are similar in most horticultural characteristics. However 'DURATAT' differs from *Guzmania* 'Allura' in the following characteristics:

1. Different flower color.

BRIEF DESCRIPTION OF THE PHOTOGRAPH

The accompanying photograph in FIG. 1 illustrates in full color a typical plant of 'DURATAT' grown in a climate controlled greenhouse in Evergem, Belgium. This plant is approximately 20 months old, shown in an 12 cm. pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'DURATAT' plants grown in a climate controlled greenhouse in Evergem, Belgium. Temperatures ranged from 18° C. to 22° C. at night to 20° C. to 28° C. during the day. No artificial light, photoperiodic or chemical treatments were given to the plants. Measurements and numerical values represent averages of typical plant types.

Botanical classification: *Guzmania* hybrid 'DURATAT'.

PROPAGATION

First propagation method: Tissue culture.

Type of propagation typically used: Tissue culture.

Time to initiate roots: About 15 days at approximately 20° C.

Time to produce a rooted cutting/liner: About 180 days at approximately 22° C.

Root description: Moderately dense, moderately branched, fine, fibrous, not fleshy, colored near RHS Brown 200A to 200D.

PLANT

Growth habit: Upright, monopodial.

Height: Average: 35.9 cm.

Plant spread: Average: 52.1 cm.

Normal pot size: 12 cm (circular).

Growth rate: Moderate.

Branching characteristics: Monopodial, leaves form a basal rosette, inflorescence grows from the center of the rosette.

Number of Leaves per scape: Average: 17.

Stem length: No stems present, scape grows directly from rosette.

FOLIAGE

Leaf:

*Arrangement*.—Rosulate; leaves (average: 17) placed in a basal rosette.

*Average length*.—Approximately 33.6 cm.

*Average width*.—Approximately 3.9 cm (measured at 50% of the leaf blade).

*Shape of blade*.—Ligulate.

*Aspect*.—Base in an average angle of 45° to horizontal, tip arching downward in an average angle of −15° (horizontal =0°), outer tip curved downward in an average angle of −120° to horizontal.

*Apex*.—Apiculate, outer tip curved downward in an average angle of −120° to horizontal.

*Base*.—Sheathing. Sheath length: Average 11.9 cm. Sheath width: Average 7.4 cm. Sheath color: Greyed-yellow, near RHS 161A to 161B.

*Margin*.—Entire.

*Texture of top surface*.—Glabrous, glossy.

*Texture of bottom surface*.—Glabrous, glossy.

*Color*.—Young foliage upper side: Green to yellow-green; in between near RHS N137A and 147A but darker. Young foliage under side: Green to yellow-green; in between near RHS N137A and 147A but slightly darker. Mature foliage upper side: Green to yellow-green; in between near RHS N137A and 147A but darker. Mature foliage under side: Green to yellow-green; in between near RHS N137A and 147A.

*Venation*.—Type: Parallel. Venation coloration: As leaf blade; upper side green to yellow-green; in between near RHS N137A and 147A but darker, under side green to yellow-green; in between near RHS N137A and 147A.

Petiole: No petioles present, leaves sheathing.

INFLORESCENCE

General description: Simple spike(scape) consisting of many bracts only. Individual flowers are not distinguishable. Flower parts are highly compressed together. Spike emerges from the center of the rosette. Inflorescence is formed by conspicuous bracts.

Inflorescence:

*Inflorescence height, excluding scape*.—Approximately 13.2 cm.

*Inflorescence width*.—Approximately 19.8 cm.

Scape:

*Length*.—Approximately 22.7 cm.

*Width*.—Approximately 0.8 cm.

*Aspect*.—Approximately 90° angle to rosette (near vertical).

*Strength*.—Very strong.

*Color*.—Yellow-green, near RHS 145C.

Bracts:

*Scape/lowermost bracts*.—Shape: Ligulate. Length: Approximately 17.4 m (excluding sheath). Width: Approximately 3.6 cm (measured at 50% of the leaf blade). Quantity: Average 9. Tip: Apiculate, outer tip curved downward in an average angle of −120° to horizontal. Base: Sheathing. Sheath length: Approximately 6.4 cm. Sheath width: Approximately 5.9 cm. Sheath color: Yellow-green; upper side near RHS 145C, under side near RHS 144C. Margin: Entire. Color upper side: Red; in between near RHS 46A and 53A, top green; near RHS N137A. Color under side: Red; near RHS 53B, top green; near RHS N137A.

Terminal bracts:

*Shape*.—Ligulate.

*Length*.—Approximately 14.8 cm (incl. sheath).

*Width*.—Approximately 3.4 cm (measured at 50% of the leaf blade).

*Quantity*.—Average 13.

*Tip*.—Apiculate to long acute, outer tip curved downward in an average angle of −10 to horizontal (=0°).

*Base*.—Sheathing. Sheath length: Approximately 5.8 cm. Sheath width: Approximately 5.5 cm. Sheath color: Yellow-green; upper side near RHS 145C, under side near RHS 144C.

*Margin*.—Entire.

*Coloration terminal bracts*.—Upper side: Red; near RHS 46B, outer tip very slightly tinged black; near RHS 203B. Under side: Red; near RHS 53B, outer tip very slightly tinged black; near RHS 203B.

Individual flower and reproductive organs: Observed flowers are less than 5 mm in length and diameter, highly compressed. Individual flower parts are indistinguishable and immeasurable, due to minute size.

OTHER CHARACTERISTICS

Disease resistance: Neither resistance nor susceptibility to the normal diseases and pests of *Guzmania* has been observed.

Drought tolerance and cold tolerance: Observed to tolerate temperatures to 40° C. without any negative effects. Temperature tolerance above this range has not been observed. Tolerance of cold temperatures has not been observed.

Fruit/seed production: No production observed to date.

What is claimed is:

1. A new and distinct cultivar of *Guzmania* plant named 'DURATAT' as herein illustrated and described.

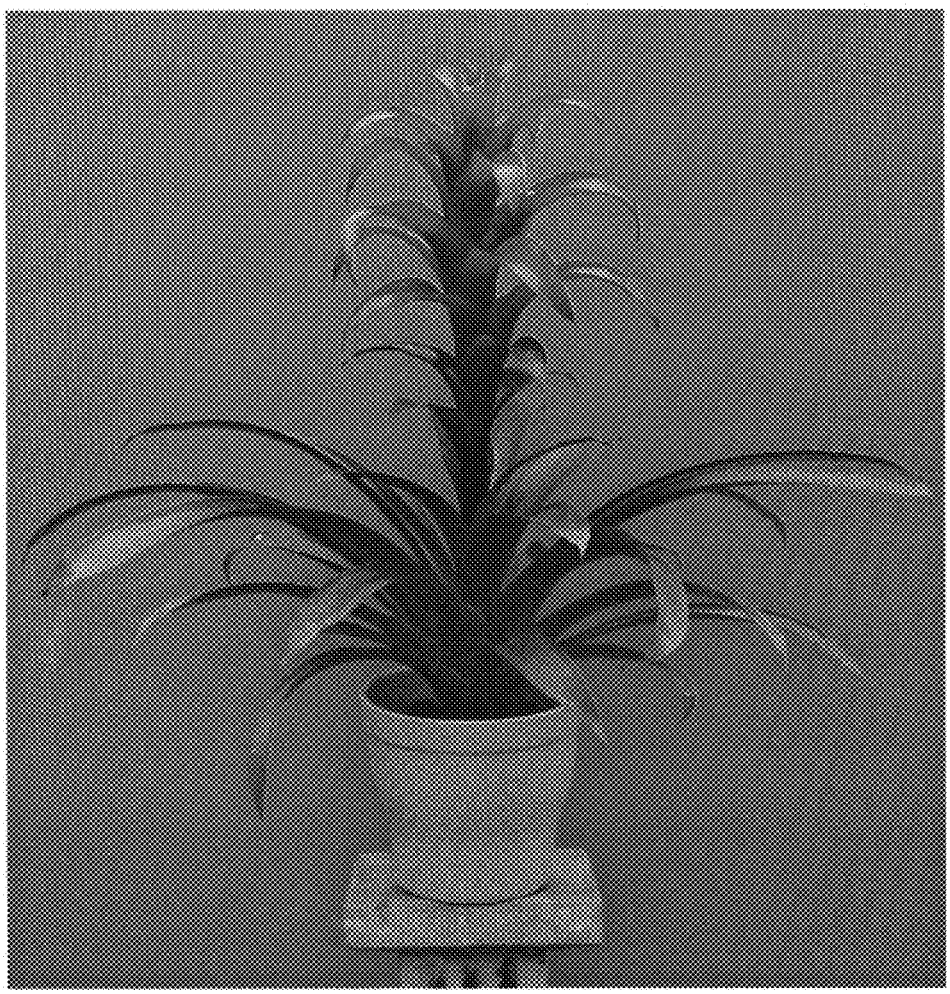

* * * * *